United States Patent [19]
Glover et al.

[11] Patent Number: 5,723,111
[45] Date of Patent: Mar. 3, 1998

[54] FOAM BOOSTING OF HAIR SHAMPOO COMPOSITIONS

[75] Inventors: David Alan Glover; Linda Moy Madore, both of Midland, Mich.

[73] Assignee: Dow Corning Corporation, Midland, Mich.

[21] Appl. No.: 161,562

[22] Filed: Dec. 6, 1993

Related U.S. Application Data

[62] Division of Ser. No. 43,338, Apr. 6, 1993.
[51] Int. Cl.$^6$ .................................................. A61K 7/075
[52] U.S. Cl. .................. 424/70.1; 424/70.11; 424/70.12; 424/70.19; 424/70.21; 424/70.27; 424/70.31; 510/122; 510/417; 252/307; 514/945
[58] Field of Search .................. 424/70, 70.1, 70.11, 424/70.12, 70.19, 70.21, 70.27, 70.31; 514/945, 63; 252/174.15, 307, DIG. 13; 510/417, 122

[56] References Cited

U.S. PATENT DOCUMENTS

| | | | |
|---|---|---|---|
| 4,879,051 | 11/1989 | Lo et al. | 252/174.15 |
| 5,057,240 | 10/1991 | Madore et al. | 252/174.15 |
| 5,075,103 | 12/1991 | Halloran et al | 424/71 |
| 5,157,139 | 10/1992 | Legrow et al. | 556/470 |

*Primary Examiner*—Raj Bawa, Ph.D.
*Attorney, Agent, or Firm*—James L. Decesare

[57] ABSTRACT

Oxyethylene functional organosilane compounds are used as foam boosters in hair shampoo compositions. The oxyethylene functional organosilane compounds having the formula $RSiR'_3$ in which R is the radical —$O(CH_2CH_2O)_xR''$; R' is an R group or an alkyl group having one to six carbon atoms; R" is an endblocking radical such as hydrogen, an alkyl group having one to six carbon atoms, or an aryl group; and x is an integer having a value of six to thirty.

6 Claims, No Drawings

FOAM BOOSTING OF HAIR SHAMPOO COMPOSITIONS

This is a divisional of copending application Ser. No. 08/043,338 filed on Apr. 6, 1993.

BACKGROUND OF THE INVENTION

This invention is directed to certain oxyethylene functional organosilane compounds, and more particularly relates to their use as foam boosters in hair shampoo compositions.

Shampoo products are expected to foam and to foam well because the consumer identifies their foaming ability and a voluminous quantity of lather with cleansing performance. In the past, this expectation has been met by the use of various organic foam boosting materials including such compounds as fatty acid amides, fatty acid alkanolamides, betaines, sulfobetaines, and amine oxides. Since some of these organic compounds have the potential for causing irritation to the human skin, a need exists for alternative foam boosting products.

Organosilicon compounds as a class have developed a reputation as being reducers of foam rather than boosters of foam, since many organosilicon based compounds have been employed as antifoams. Therefore, it is quite unexpected and unique in accordance with the teaching of the present invention to discover a certain category of organosilicon compound which possesses the capability of performing a function opposite to its expected function.

Thus, the present invention provides an oxyethylene functional organosilane as a foam booster and a foam builder for hair shampoo applications. Incorporation of such compounds in hair shampoo formulations has been found to increase the amount of foam available from a given system.

SUMMARY OF THE INVENTION

This invention involves the boosting of foam, and to the method of increasing the volume of foam produced in the use of hair shampoos by employing an oxyethylene functional organosilane as the foam boosting or foam building additive in the shampoo formulation. Along with its foam boosting capability, the oxyethylene functional organosilane has also been found to provide a foam that is more dense, more stable, and which has a more creamy conditioning feel. Shampoo formulations containing the oxyethylene functional organosilane further are capable of contributing a light conditioning effect to the hair.

These and other features, advantages and objects of the herein defined present invention will become more apparent when considered in light of the following detailed description thereof.

DETAILED DESCRIPTION OF THE INVENTION

A foam booster is an agent which increases the amount of foam available from a system at a constant molar concentration of surfactant, in contrast to a foam stabilizer which delays the collapse of a foam. Foam building is provided in accordance with the present invention in an aqueous media containing an anionic surfactant, a cationic surfactant, and a nonionic surfactant, by adding to the aqueous media, a foam boosting effective amount of a foam boosting compound which is an oxyethylene functional organosilane compound.

The organosilane compound has the formula $RSiR'_3$ in which R is the radical $-O(CH_2CH_2O)_xR''$. R' can be an R group or an alkyl group having one to six carbon atoms. R" can be an endblocking group such as hydrogen; an alkyl group having one to six carbon atoms such methyl, ethyl, propyl, and butyl; and an aryl group such as phenyl and benzyl. The integer x can have a value of from about six to about thirty, but preferably x has a value of from twelve to twenty. Among one of the most preferred compounds according to the present invention, and the compound which was used in the examples set forth below, is an oxyethylene functional organosilane compound of the formula $(CH_3)_2Si[O(CH_2CH_2O)_{16}H]_2$.

These organosilane compounds may be prepared by the reaction of a disilazane or a cyclic silazane with an organic monohydric, dihydric, or polyhydric alcohol, in the presence of an inorganic catalyst such as sulfuric acid or phosphoric acid. Such methods of preparation are described in detail for example in U.S. Pat. No. 5,157,139 which issued Oct. 20, 1992, and which patent is incorporated herein by reference thereto.

Shampoos capable of generating a greater volume of foam may be produced in accordance with the concepts of the present invention by combining 10 to 80 percent by weight of water, preferably about 30 to 50 percent by weight; 10 to 50 percent by weight of a surfactant which can be one or a mixture of one or more anionic, cationic, nonionic, and amphoteric emulsifying agents, preferably about 15 to 30 percent by weight; 0.1 to 10 percent by weight of a cationic conditioning agent, preferably about 3 to 5 percent by weight; 0.1 to 1.0 percent by weight of suitable preservative; 0.1 to 2.0 percent by weight of a thickening agent; 0.1 to 10 percent by weight of the oxyethylene functional organosilane foam boosting compound, preferably about 3 to 5 percent by weight; 0.1 to 1.0 percent by weight of a fragrance; and 0.1 to 2.0 percent by weight of a pH adjusting agent.

The hair treating compositions of the present invention may contain a surfactant such as an anionic, amphoteric, nonionic, or cationic emulsifying agent, and mixtures of such emulsifying agents. The surfactant should provide an acceptable level of foam on the hair and be capable of cleaning the hair.

Suitable anionic surfactants include sulfonated and sulfated alkyl, aralkyl, and alkaryl anionic detergents such as alkyl succinates, alkyl sulfosuccinates, and N-alkyl sarcosinates. Representative detergents are the sodium, magnesium, ammonium, and the mono-, di-, and triethanolamine salts of alkyl and aralkyl sulfates, as well as the salts of alkaryl sulfonates. The alkyl groups of the detergents should have a total of from twelve to about twenty-one carbon atoms, and may be unsaturated. Fatty alkyl groups are preferred. The sulfates may be sulfate ethers containing one to ten ethylene oxide or propylene oxide units per molecule, with two to three ethylene oxide units being sufficient for most purposes.

Typical anionic detergents are sodium lauryl sulfate, sodium lauryl ether sulfate, ammonium lauryl sulfate, triethanolamine lauryl sulfate, sodium C14-16 olefin sulfonate, ammonium C12-15 pareth sulfate, sodium myristyl ether sulfate, ammonium lauryl ether sulfate, disodium monooleamidosulfosuccinate, ammonium lauryl sulfosuccinate, sodium dodecylbenzene sulfonate, triethanolamine dodecylbenzene sulfonate, and sodium N-lauryol sarcosinate.

Among the various surfactants classified as amphoteric or ampholytic which may be used are cocoamphocarboxyglycinate, cocoamphocarboxypropionate, cocobetaine, N-cocamidopropyldimethylglycine, and N-lauryl-N-carboxymethyl-N-(2-hydroxyethyl)ethylenediamine. Other suitable amphoteric detergents which may be used include betaines and sultaines.

Betaines may have the formula R'R"R'"N$^+$(CH$_2$)$_m$COO$^-$ in which R' is an alkyl group having twelve to eighteen carbon atoms and mixtures thereof; R" and R'" are lower alkyl groups of one to three carbon atoms; and m has a value of one to four. Specific compounds may include alpha-(tetradecyldimethylammonio)acetate, beta-(hexadecyldiethylammonio)propionate, and gamma-(dodecyldimethylammonio)butyrate.

Sultaines may have the formula R'R"R'"N$^+$(CH$_2$)$_m$SO$_3^-$ in which R', R", R'", and m, are the same as defined above. Specific compounds may include 3-(dodecyldimethylammonio)-propane-1-sulfonate, and 3-(tetradecyldimethylammonio)ethane-1-sulfonate.

Nonionic surfactants suitable for use in the hair treating compositions of the present invention can be fatty acid alkanolamides and amine oxide surfactants. Representative fatty acid alkanolamides include fatty acid diethanolamides such as isostearic acid diethanolamide, lauric acid diethanolamide, capric acid diethanolamide, coconut fatty acid diethanolamide, linoleic acid diethanolamide, myristic acid diethanolamide, oleic acid diethanolamide, and stearic acid diethanolamide. Suitable fatty acid monoethanolamides include coconut fatty acid monoethanolamide. Fatty acid monisopropanolamides which may be used are oleic acid monoisopropanolamide and lauric acid monoisopropanolamide.

Amine oxide nonionic surfactants suitable for use in the present invention are N-alkyl amine oxides such as N-cocodimethylamine oxide, N-lauryl dimethylamine oxide, N-myristyl dimethylamine oxide, and N-stearyl dimethylamine oxide. Suitable N-acyl amine oxides are N-cocoamidopropyl dimethylamine oxide and N-tallowamidopropyl dimethylamine oxide. N-alkoxyalkyl amine oxides such as bis(2-hydroxyethyl) C12-15 alkoxypropylamine oxide may also be employed. The hydrophobic portion of the amine oxide surfactant should be provided by a fatty hydrocarbon chain of about ten to twenty-one carbon atoms.

Cationic surfactants useful in the compositions of the present invention may include those compounds which contain amino or quaternary ammonium hydrophilic moieties in the molecule which are positively charged, such as quaternary ammonium salts. Representative of the various quaternary ammonium salts which may be employed are ditallowdimethyl ammonium chloride, ditallowdimethyl ammonium methyl sulfate, dihexadecyl dimethyl ammonium chloride, di(hydrogenated tallow) dimethyl ammonium chloride, dioctadecyl dimethyl ammonium chloride, dieicosyl dimethyl ammonium chloride, didocosyl dimethyl ammonium chloride, di(hydrogenated tallow) dimethyl ammonium acetate, dihexadecyl dimethyl ammonium acetate, ditallow dipropyl ammonium phosphate, ditallow dimethyl ammonium nitrate, di(coconutalkyl) dimethyl ammonium chloride, and stearyl dimethyl benzyl ammonium chloride.

The hair treating compositions of the invention may contain other adjuvants to provide a product which is aesthetically pleasant to the consumer such as thickeners, perfumes, colorants, electrolytes, pH control agents, foam boosters and builders, foam stabilizers, antimicrobials, antioxidants, ultraviolet light absorbers, and medicaments.

Thickeners are used to facilitate the hand application of the composition to the hair, and are added in sufficient quantities to provide a more luxurious effect. Hair care compositions with viscosities in the range of six thousand to twelve thousand centistokes measured at twenty-five degrees Centigrade, are generally sufficient. Representative thickening agents which may be used are sodium alignate; gum arabic; guar gum; hydroxypropyl guar gum; cellulose derivatives such as methylcellulose, hydroxypropyl methylcellulose, hydroxyethylcellulose, and hydroxypropylcellulose; starch and starch derivatives such as hydroxyethylamylose and starch amylose; locust bean gum; electrolytes such as sodium chloride and ammonium chloride; saccharides such as fructose and glucose; and derivatives of saccharides such as PEG-120 methyl glucose dioleate.

Only cosmetically acceptable perfumes and fragrances should be used to prepare the composition. Colorants may be added where it is desired to confer a hue to the composition. An acid may be employed to adjust the pH within the range of about five to nine. Any water soluble carboxylic acid or mineral acid may be employed. Suitable compounds include mineral acids such as hydrochloric acid, sulfuric acid, and phosphoric acid; monocarboxylic acids such as acetic acid, lactic acid, and propionic acid; and polycarboxylic acids such as succinic acid, adipic acid, and citric acid.

Additional conditioners may be added to the composition in the form of organic cationic conditioning agents for the purpose of providing hair grooming. Such cationic conditioning agents may include quaternary nitrogen derivatives of cellulose ethers; homopolymers of dimethyldiallyl ammonium chloride; copolymers of acrylamide and dimethyldiallyl ammonium chloride; homopolymers or copolymers derived from acrylic acid or methacrylic acid which contain cationic nitrogen functional groups attached to the polymer by ester or amide linkages; polycondensation products of N,N'-bis-(2,3-epoxypropyl)-piperazine or piperazine-bis-acrylamide and piperazine; and copolymers of vinylpyrrolidone and acrylic acid esters with quaternary nitrogen functionality.

Cationic surfactants such as cetyl trimethylammonium chloride, cetyl trimethylammonium bromide, and stearyltrimethylammonium chloride, may also be employed in the compositions as a cationic conditioning agent.

A preservative may be required and representative compounds which may be employed include formaldehyde, DMDM hydantoin, 5-bromo-5-nitro-1,3-dioxane, methyl paraben, propyl paraben, sorbic acid, diazolidinyl urea, and imidazolidinyl urea.

The following examples are set forth for the purpose of illustrating the invention in more detail.

EXAMPLE I

A crystal clear high foaming mild conditioning Shampoo "A" was prepared by combining the ingredients shown in Table I. Shampoo "A" contained the oxyethylene functional organosilane, whereas the silane was omitted from Shampoo "B" for purposes of comparison. Shampoos "A" and "B" were prepared by heating the water portion of the formulation to seventy degrees Centigrade, and adding the remaining ingredients in the order in which they are listed in Table I. The combination of ingredients was mixed until uniform and cooled to room temperature.

TABLE I

| Ingredient | Conditioning Shampoo (Weight Percent) | |
|---|---|---|
| | Shampoo "A" | Shampoo "B" |
| 1. Deionized Water | 37.7 | 37.7 |
| 2. Sodium Lauryl Ether Sulfate (Anionic Surfactant) | 22.0 | 22.0 |
| 3. Ammonium Lauryl Ether Sulfate (Anionic Surfactant) | 18.0 | 18.0 |
| 4. Cocamidopropylbetaine (Amphoteric Surfactant) | 10.0 | 10.0 |
| 5. Lauramide DEA (Nonionic Surfactant) | 6.0 | 6.0 |
| 6. Citric Acid (50%) (pH Adjusting Agent) | 1.0 | 1.0 |
| 7. Fragrance | 0.1 | 0.1 |
| 8. DMDM Hydantoin (Preservative) | 0.2 | 0.2 |
| 9. Oxyethylene Organosilane (Foam Boosting Agent) | 5.0 | — |
| 10. Deionized Water | — | 5.0 |

EXAMPLE II

Shampoos "A" and "B" were tested for their tendency to foam by the measurement of the volume of foam generated under shear conditions. The foam volume was determined by measuring the foam after blending a test fluid for ten seconds in a Waring commercial 7-speed Blendor. The procedure used was a modified version of the standard Ross-Miles Test DIN 53902 (Deutsche Industrie Norm-Federal Republic of Germany). Fifty milliliters of test fluid was employed. The test fluids used were ten percent solutions of each of Shampoos "A" and "B" in deionized water. The foam volume for Shampoo "A" was 260 milliliters, whereas the foam volume of Shampoo "B" was only 205 milliliters.

Thus, Shampoo "A" which contained the oxyethylene functional organosilane of the invention, generated some fifty-five more milliliters of foam than Shampoo "B", which can be seen to be a significant improvement in performance. The foam of Shampoo "A" was also noted to be thicker and to provide a more dense lather than the foam of Shampoo "B".

EXAMPLE II

A hair conditioner was prepared for the purpose of illustrating the compatibility and water solubility of the oxyethylene functional organosilane of the present invention. This after-shampoo hair rinse conditioner was prepared by combining the ingredients shown in Table II. The ingredients were added together in the order listed in Table II at room temperature and mixed until uniform. The hair conditioner was noted to be crystal clear by visual observation.

TABLE II

| Ingredients | Hair Rinse Conditioner (Weight Percent) |
|---|---|
| 1. Deionized Water | 78.79 |
| 2. Acetamide DEA (Nonionic Surfactant) | 5.00 |
| 3. Cetrimonium Bromide (Cationic Surfactant) | 4.00 |
| 4. Polyquaternium 7 (Cationic Surfactant) | 1.00 |

TABLE II-continued

| Ingredients | Hair Rinse Conditioner (Weight Percent) |
|---|---|
| 5. Quaternium 26 (Cationic Surfactant) | 2.00 |
| 6. PEG 75 Lanolin (Nonionic Surfactant) | 1.00 |
| 7. Hydrolyzed Collagen (Conditioning Agent) | 3.00 |
| 8. DMDM Hydantoin (Preservative) | 0.20 |
| 9. Menthol (Fragrance) | 0.01 |
| 10. Oxyethylene Organosilane | 5.00 |

EXAMPLE III

A hair conditioner capable of providing conditioning benefits to rinse conditioning emulsion formulations was prepared by combining the ingredients shown in Table III. The water portion of the formulation was heated to seventy degrees Centigrade and the thickening agent was sifted into the water accompanied with mixing. The remaining ingredients were added in the order listed in Table III and mixed until uniform. The hair conditioner was cooled to room temperature.

TABLE III

| Ingredients | Hair Conditioner (Weight Percent) |
|---|---|
| 1. Deionized Water | 89.7 |
| 2. Hydroxyethylcellulose (Thickening Agent) | 0.5 |
| 3. Stearalkonium Chloride (Cationic Surfactant) | 3.0 |
| 4. Glyceryl/PEG 100 Stearate (Nonionic Surfactant) | 1.0 |
| 5. Cetyl Alcohol (Nonionic Surfactant) | 0.5 |
| 6. Fragrance | 0.1 |
| 7. DMDM Hydantoin (Preservative) | 0.2 |
| 8. Oxyethylene Organosilane | 5.0 |

Other variations and modifications may be made in the compounds, compositions, and methods, described herein without departing from the essential features and concepts of the present invention. The forms of the invention described herein are exemplary only and are not intended as limitations on the scope of the invention as defined in the appended claims.

That which is claimed is:

1. A shampoo composition comprising 10 to 80 percent by weight of water; 10 to 50 percent by weight of an emulsifying agent selected from the group consisting of an anionic surfactant, a cationic surfactant, a nonionic surfactant, an amphoteric surfactant, and mixtures thereof, and 0.1 to 10 percent by weight of a foam boosting compound which is an oxyethylene functional organosilane having the formula $RSiR'_3$ in which R is the radical $-O(CH_2CH_2O)_xR''$; R' is an R group or an alkyl group having one to six carbon atoms; R" is a radical selected from the group consisting of hydrogen, an alkyl group having one to six carbon atoms, and an aryl group; and x is an integer having a value of six to thirty.

2. A shampoo according to claim 1 which further includes 0.1 to 10 percent by weight of a cationic conditioning agent.

3. A shampoo according to claim 2 which includes 30 to 50 percent by weight of water, 15 to 30 percent by weight of a mixture of surfactants; and 3 to 5 percent by weight of the cationic conditioning agent.

4. A shampoo according to claim 3 which includes 3 to 5 percent by weight of the oxyethylene functional organosilane.

5. A shampoo according to claim 1 in which the value of the integer x is from twelve to twenty.

6. A shampoo according to claim 5 in which the oxyethylene functional organosilane has the formula $(CH_3)_2Si[O(CH_2CH_2O)_{16}H]_2$.

* * * * *